United States Patent
Turner et al.

(10) Patent No.: US 7,822,276 B2
(45) Date of Patent: Oct. 26, 2010

(54) METHOD AND APPARATUS FOR ANALYZING BODY FLUIDS

(75) Inventors: Richard H. Turner, Mercer Island, WA (US); Eric Chapoulaud, Pasadena, CA (US)

(73) Assignee: IRIS International, Inc., Chatsworth, CA (US)

( * ) Notice: Subject to any disclaimer, the term of this patent is extended or adjusted under 35 U.S.C. 154(b) by 1202 days.

(21) Appl. No.: 11/354,603

(22) Filed: Feb. 14, 2006

(65) Prior Publication Data

US 2006/0192113 A1     Aug. 31, 2006

Related U.S. Application Data

(60) Provisional application No. 60/653,752, filed on Feb. 17, 2005.

(51) Int. Cl.
*G06K 9/46* (2006.01)
*G06K 9/00* (2006.01)
*E03B 1/00* (2006.01)
*C12Q 1/00* (2006.01)

(52) U.S. Cl. .................... 382/192; 382/128; 137/7; 435/4

(58) Field of Classification Search ............ 382/192, 382/128; 435/4; 137/1
See application file for complete search history.

(56) References Cited

U.S. PATENT DOCUMENTS

| 4,338,024 | A | | 7/1982 | Bolz |
| 4,393,466 | A | | 7/1983 | Deindoerfer |
| 4,612,614 | A | | 9/1986 | Deindoerfer |
| 4,667,335 | A | | 5/1987 | Deindoerfer |
| 4,861,728 | A | * | 8/1989 | Wagner ..................... 436/501 |
| 5,822,447 | A | * | 10/1998 | Kasdan ..................... 382/133 |
| 6,794,203 | B2 | * | 9/2004 | Chen et al. ................. 438/14 |
| 7,152,616 | B2 | * | 12/2006 | Zucchelli et al. ......... 137/68.11 |
| 2003/0018007 | A1 | * | 1/2003 | Gregory et al. .............. 514/44 |
| 2004/0126008 | A1 | | 7/2004 | Chapoulaud |
| 2004/0136593 | A1 | | 7/2004 | Chapoulaud |
| 2006/0073470 | A1 | * | 4/2006 | Noda et al. ..................... 435/4 |
| 2007/0116704 | A1 | * | 5/2007 | Goletz et al. ............. 424/145.1 |

* cited by examiner

*Primary Examiner*—Bhavesh M Mehta
*Assistant Examiner*—Kathleen S Yuan
(74) *Attorney, Agent, or Firm*—DLA Piper LLP (US)

(57) ABSTRACT

A system and method for analyzing a specimen containing particles that can be difficult to differentiate. The system and method determines a first collective count of a selected group of particles in the specimen, treats at least a portion of the specimen to alter a subgroup of the selected group of particles, determines a second collective count of any of the selected group of particles in the treated portion of the specimen, and subtracts the second collective count from the first collective count to determine a differentiation count for the subgroup of particles altered by the treating of the specimen. The system and method is described with the example of determining concentrations of red and white blood cells in a specimen (e.g. spinal fluid), using auto-particle recognition techniques, without attempting to distinguish and count red versus white blood cells co-existing in the same specimen portion.

9 Claims, 3 Drawing Sheets

METHOD AND APPARATUS FOR ANALYZING BODY FLUIDS

RELATED APPLICATION

This application claims the benefit of U.S. Provisional Application Ser. No. 60/653,752 filed on Feb. 17, 2005, the content of which is hereby incorporated by reference in its entirety.

FIELD OF THE INVENTION

The present invention relates generally to methods and systems for analyzing particles in a sample and more particularly for identifying and quantifying the particles in the sample.

BACKGROUND OF THE INVENTION

Methods and apparatuses for processing images of particles in a fluid sample are well known. For example, U.S. Pat. Nos. 4,338,024, 4,393,466, 4,667,335 and 4,612,614 describe apparatuses for analyzing biological particles. Such biological particle analysis apparatuses can automatically—i.e., without human intervention—determine characteristics such as color, size, and brightness of particles in a fluid sample. Moreover, based on the determined characteristics, these apparatuses can categorize each particle into one of many classes and calculate the concentration of each particle type (i.e., particle class). This automatic sample analysis and concentration determination process is referred to as Auto-Particle Recognition (APR).

The classification and calculation results can be displayed in the manner disclosed in U.S. Pat. No. 5,822,447. Namely, a plurality of optical frames are taken, wherein each frame is a picture of a portion of the sample. Preferably, the frames represent different portions of the sample. A frame is made of one or more "patches" of images, with each patch containing at least one particle image. Patch recognition can be implemented according to U.S. Patent Application Publication 2004/0136593. The patches are classified into one of a plurality of classes based on the images they contain, and the classes are usually characterized by one or more visually discernible characteristics. In some embodiments, if a patch contains more than one discernable particle image, the particle images could be classified separately. In other embodiments, the image of the more predominant particle is used to classify the patch. Neural network technology can be utilized in the automated classification process, such as disclosed in U.S. Patent Application Publication 2004/0126008. After the classification, the concentrations of each class of particles are determined.

The patches extracted from the frames can displayed on a graphical user interface (e.g., a computer monitor), preferably in an ordered array by classification. The number of particles within each class, or any parameter derived therefrom (e.g., a percentage of the total number of particles), may be displayed. The APR process determines the concentration (i.e. otherwise referred to as the count, which is the number of particles per unit volume of the specimen) of each particle type (i.e., particle class) based on this classification. Then, an operator can manually review the APR classification results and correct any errors. During the manual review process, the operator may pull a misclassified particle out of one class and add it to another class.

One application for APR is counting red blood cells (RBCs) and white blood cells (WBCs) (otherwise known as lymphocytes) from a spinal fluid specimen. The problem is that for some APR systems, it can be difficult to accurately discriminate between and quantify RBCs and WBCs. There is a need for a system and method for improved particle classification.

SUMMARY OF THE INVENTION

Disclosed herein is a method and system for improving the accuracy of auto-particle recognition and analysis.

A method of analyzing a specimen containing particles includes determining a first collective count of a selected group of particles in the specimen, treating at least a portion of the specimen to alter a subgroup of the selected group of particles, determining a second collective count of any of the selected group of particles in the treated portion of the specimen, and subtracting the second collective count from the first collective count to determine a differentiation count for the subgroup of particles altered by the treating of the specimen.

A device for analyzing a specimen containing particles that includes an imaging device for capturing images of treated and untreated portions of a specimen and creating electronic images from the captured images, wherein a subgroup of a selected group of particles of the specimen is altered in the treated portion of the specimen, and a processor. The processor is adapted to determine a first collective count of the selected group of particles in the untreated portion of the specimen, determine a second collective count of any of the selected group of particles in the treated portion of the specimen, and subtract the second collective count from the first collective count to determine a differentiation count for the subgroup of particles altered in the treated portion of the specimen.

Other objects and features of the present invention will become apparent by a review of the specification, claims and appended figures.

DETAILED DESCRIPTION OF THE PREFERRED EMBODIMENTS

Figure 1:
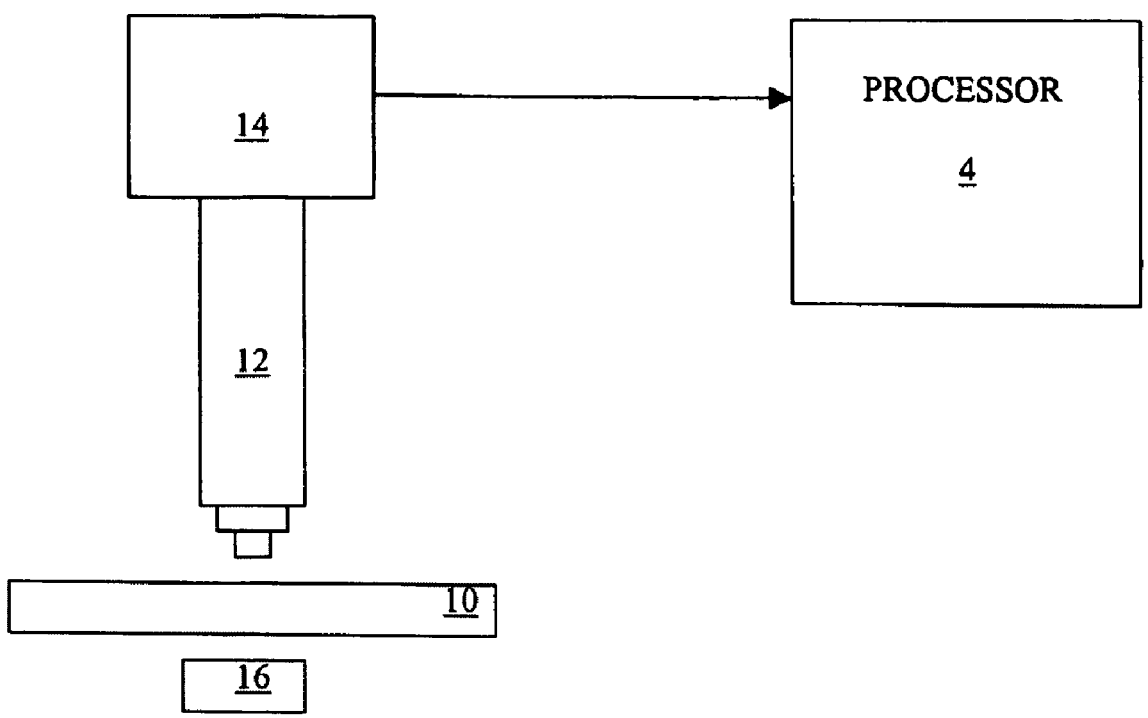
FIG. 1 is a schematic diagram of a particle analyzer.

The system and method described herein enhances classification accuracy for particles that can be difficult to differentiate between, especially in automated particle analyzer systems. The enhanced system and method can be employed using Auto-Particle Recognition (APR) techniques employing a particle analyzer having an imaging system 2 and a processor 4, as schematically illustrated in FIG. 1.

Imaging System and Processor

Imaging system 2 is used to produce images of fields of view of a sample containing the particles of interest. Imaging system 2 is preferably a well known flow microscope, such as those described in U.S. Pat. Nos. 4,338,024, 4,393,466, 4,538,299 and 4,612,614, which are all hereby incorporated herein by reference. Such a system includes a flow cell 10, a microscope 12, and a camera 14, as shown in FIG. 1. Specimen fluid containing the particles of interest is passed through an examination area of the flow cell 10, whereby images of the particles are viewable through the flow microscope 12. The camera 14 (which is preferably a CCD camera) captures images of successive fields of view of the particles via the microscope 12, as the particles flow through the flow cell 10, and converts them to digital particle images. Each of the digital particle images taken by the camera 14 comprise thousands or even millions of individual pixels. A light source 16 (e.g. strobe) is preferably used to illuminate (by front and/or back lighting) the examination area of the flow cell 10. It should be noted that the method and system described herein can also be applied to an imaging method and system that analyzes non-flowing specimen fluid (e.g. specimen fluid placed on an examination slide).

Processor 4 can be any microprocessor and/or computer system, or a plurality of microprocessors and/or computer systems, capable of processing the digital particle images as described below. Examples of such processors include, but are not limited to, data processors, DSP's (digital signal processors), microcontrollers, and computer system processors, each of which can be CISC and/or RISC type. The processor 4 processes the digital particle images to detect, classify, quantify, and/or display images of the particles, preferably using some or all of the techniques disclosed in U.S. Pat. Nos. 4,338,024, 4,393,466, 4,667,335 and 4,612,614, and 5,822, 44, and U.S. Patent Application Publications 2004/0136593 and 2004/0126008, all of which are incorporated herein by reference.

Enhanced Particle Detection

Figure 2:
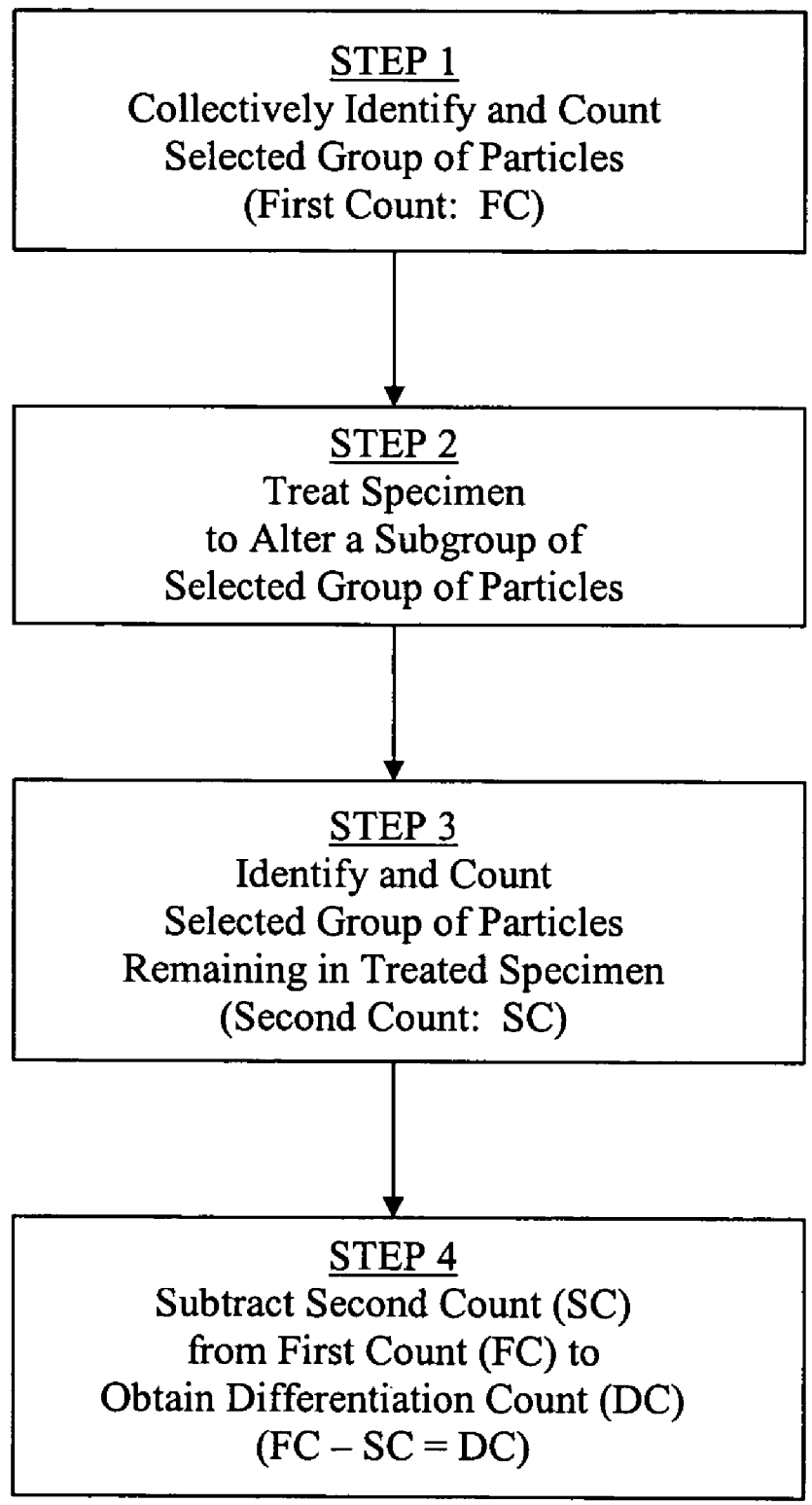
FIG. 2 is a flow chart showing the method steps of one embodiment of particle analysis.

The processor 4 described above includes further functionality to perform the method described below and in FIG. 2, which enhances the accuracy of counting particles that are difficult to distinguish from each other. As used herein, "count" or "counting" shall mean the determination of the number of particles of interest in a known volume of specimen fluid or in a unit volume of specimen fluid. The method is described with respect to red blood cells (RBCs) and white blood cells (WBCs) in a specimen such as spinal fluid, as an example only. However, other hard to distinguish particles can be classified and counted in a similar manner in other fluid specimens, and the claims should not necessarily be limited in any way to spinal fluid specimens for quantifying RBCs and WBCs based on this example.

In Step 1, a selected group of particles (e.g. RBCs and WBCs) in the specimen are collectively identified and counted by subjecting a fraction of the specimen to conventional APR techniques, resulting in a first count value FC. This first count FC represents the total particle count of all particles in the selected group present in the specimen (e.g. total count of red and white blood cells in the specimen). At this step, there is no need to attempt a differentiation between the different particle types in the selected group of particles (e.g. no need to attempt separate counts of RBCs and WBCs at this time).

In Step 2, a fraction of the specimen is treated so that a subgroup of one or more particle types from the selected group of particles is altered (e.g. changed, disintegrated, destroyed, or otherwise removed from the specimen) so that the APR technique used to identify the group of selected particles no longer recognizes and counts the subgroup of particles. In the case of a specimen with RBCs and WBCs, the specimen is treated with a lysin agent, with destroys the RBCs in the specimen, leaving just WBC's from the selected group of particles. The APR technique for collectively counting RBCs and WBCs no longer recognizes and counts the destroyed RBCs.

In Step 3, a second count is performed on the treated specimen fraction using conventional APR techniques to identify and count the particles in the selected group of particles remaining in the treated specimen (e.g. WBCs), resulting in a second count value SC. This second count SC represents the total particle count of just those particles in the original selected group of particles that remain in the specimen after the treatment step 2 (e.g. total count of just the WBC's in the specimen). In the case of a selected group of RBCs and WBC's, there are no RBC's left in the specimen that could erroneously be identified as, and included in the count of, WBCs. Thus, the second count SC more accurately represents the actual count of WBCs in the original specimen. In many cases, this WBC count is far more accurate than APR techniques that try to distinguish these two types of particles existing together in the analyzed specimen.

In Step 4, the second count SC is subtracted from the first count FC, resulting in a differentiation count DC that accurately represents the particle count of particles that were altered in the specimen by Step 2. In the case of a selected group of RBCs and WBCs, the differentiation count DC accurately represents the RBC count in the original specimen.

The above technique of collectively counting a group of selected particles, treating the specimen to alter a subgroup of those particles, counting the remaining particles in the selected particle group, and subtracting the two count results, provides far more accurate particle counts for both the particles that were altered by specimen treatment as well as for the particles that remained in the specimen after the specimen treatment. Further, the APR techniques employed need only be able to accurately and collectively identify and count particles in a group of selected particles, without having to employ techniques that try to distinguish particles within the group of selected particles. In the case of a specimen with RBCs and WBCs, an accurate count of both these types of particles can be made without employing any APR technique that attempts to distinguish between these two types of particles co-existing in the specimen. In fact, the same APR process can be employed in both Steps 1 and 3, neither of which needing to distinguish between red or white blood cells. Thus, the above method is ideal for distinguishing between and counting particles that are more easily differentiated by specimen treatment than by APR identification techniques.

The above method is described with respect to a selected group of particles having two members: RBCs and WBCs. However, other hard to distinguish particles can be classified and counted in a similar manner. Furthermore, not only can the particle types vary as well as the number of particle types in the selected group, but the number of count and treatment steps can vary to give additional information about more complex specimens. For example, if the selected group of particles has 5 members, there could be multiple treatment steps (e.g. Step 2) affecting different particle members differently, followed by multiple identification/counting steps (e.g. Step 3). Moreover, different fractions from the same original specimen can be utilized for different steps of the method (e.g. fraction of specimen used for Steps 2 and 3 different from fraction of specimen used for Step 1), or the same fraction can be repeatedly used for multiple steps (e.g. fraction of specimen used for Steps 2 and 3 same as fraction used for Step 1).

Figure 3:
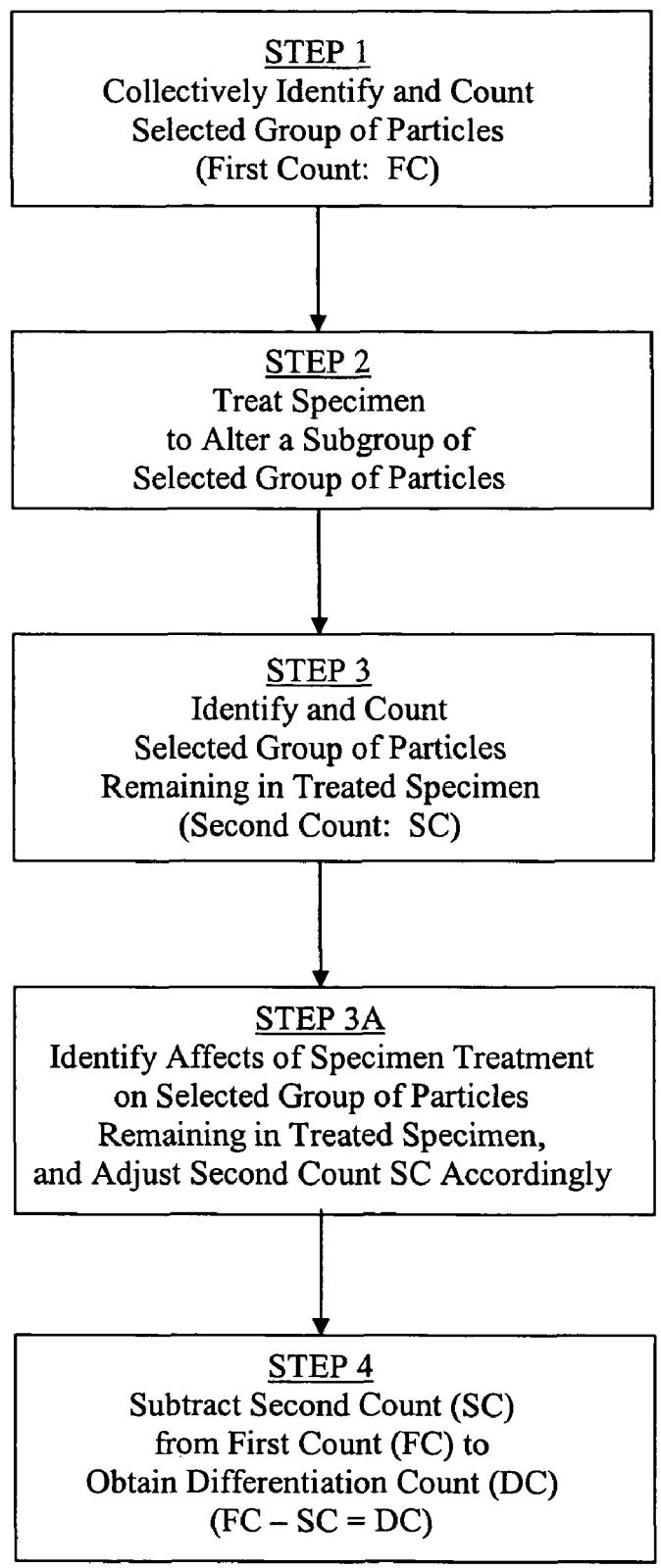
FIG. 3 is a flow chart showing the method steps of a second embodiment of particle analysis.

FIG. 3 illustrates an alternate embodiment of the above described method, whereby the second count SC can be modified in light of the affect the treatment step has on the specimen. Using the RBC and WBC example, it may be the case for some specimens that the lysin agent used to destroy the RBCs also damages or otherwise alters some of the WBCs, thus causing an under-counting of WBCs in Step 3 of FIG. 2. To remedy this situation, Step 3A is added to the process of FIG. 2, as illustrated in FIG. 3. Step 3A involves the examination of how the specimen treatment affects the particles intended to remain in the specimen after treatment, and adjusting the second count SC accordingly. In the case of a specimen with RBCs and WBCs, Step 3A would involve analyzing the specimen both before and after the lysin treatment of Step 2, and quantify how many WBCs are compromised to the point that the APR counting technique of Step 3 would not properly identify and count them as present. Step 3A would then conclude by adding this value (of compromised WBCs) to the second count value SC. The analysis in Step 3 can be performed manually by an operator and/or by other techniques once, and extrapolated to all other specimens of the same type that would be equally affected by the treatment involved.

Although embodiments have been described in detail hereinabove, it should be clearly understood that many variations and/or modifications of the basic inventive concepts herein taught fall within the spirit and scope of the present invention. For example, the APR techniques of Steps 1 and 3 of FIG. 1 can be identical, or can be varied. Additionally, the specimen need not always, or ever, necessarily be in fluid form.

What is claimed is:

1. A method of analyzing a specimen containing particles, comprising:
    determining a first collective count of a selected group of particles in a first fraction of the specimen from electronic images of the first fraction generated by an imaging device;
    treating a second fraction of the specimen different from the first fraction to alter a subgroup of the selected group of particles;
    determining a second collective count of any of the selected group of particles in the second fraction of the specimen from electronic images of the second fraction generated by the imaging device; and
    using a processor to subtract the second collective count from the first collective count to determine a differentiation count for the subgroup of particles altered by the treating of the specimen;
    determining an effect of the treating of the specimen on particles of the selected group of particles other than the subgroup of the selected group of particles; and
    adjusting the second collective count to compensate for the determined effect of the treating of the specimen.

2. The method of claim 1, wherein the determining of the first collective count comprises:
    creating the electronic images of the first fraction of the specimen; and
    collectively identifying and counting images of the selected group of particles in the electronic images of the first fraction.

3. The method of claim 2, wherein the determining of the second collective count comprises:
    creating the electronic images of the second fraction of the specimen; and
    collectively identifying and counting images of any of the selected group of particles in the electronic images of the second fraction.

4. The method of claim 3, wherein the creating of the electronic images of the first fraction further comprises:
    passing the first fraction of the specimen through a flow cell; and
    capturing images of the first fraction of the specimen in the flow cell using a camera.

5. The method of claim 4, wherein the creating of the electronic images of the second fraction further comprises:
    passing the second fraction of the specimen through the flow cell; and
    capturing images of the second fraction of the specimen in the flow cell using the camera.

6. The method of claim 1, wherein the adjusting of the second collective count is performed before the subtracting of the second collective count from the first collective count.

7. The method of claim 1, wherein:
    the selected group of particles comprises red bloods cells and white blood cells; and
    the subgroup of the selected group of particles comprises red blood cells.

8. The method of claim 7, wherein the treating comprises treating the second fraction of the specimen with a lysin agent.

9. The method of claim 8, wherein the specimen is spinal fluid.

* * * * *